(12) United States Patent
Hudak et al.

(10) Patent No.: US 9,274,056 B2
(45) Date of Patent: Mar. 1, 2016

(54) USE OF NON-CHELATED FLUOROCHROMES IN RAPID TEST SYSTEMS

(76) Inventors: Robert Hudak, San Diego, CA (US); Ian Buchanan, San Diego, CA (US)

(*) Notice: Subject to any disclaimer, the term of this patent is extended or adjusted under 35 U.S.C. 154(b) by 1232 days.

(21) Appl. No.: 12/315,413

(22) Filed: Dec. 3, 2008

(65) Prior Publication Data

US 2009/0142856 A1 Jun. 4, 2009

Related U.S. Application Data

(60) Provisional application No. 61/005,301, filed on Dec. 3, 2007.

(51) Int. Cl.
*G01N 33/558* (2006.01)
*G01N 21/64* (2006.01)
*G01N 21/84* (2006.01)
*G01N 33/58* (2006.01)

(52) U.S. Cl.
CPC .......... *G01N 21/6428* (2013.01); *G01N 21/645* (2013.01); *G01N 21/8483* (2013.01); *G01N 33/558* (2013.01); *G01N 33/582* (2013.01); *G01N 2201/062* (2013.01); *G01N 2201/0693* (2013.01); *G01N 2201/0696* (2013.01)

(58) Field of Classification Search
USPC .................................... 436/514, 518; 435/7.1
See application file for complete search history.

(56) References Cited

U.S. PATENT DOCUMENTS

| | | | |
|---|---|---|---|
| 4,703,017 A | 10/1987 | Campbell | 463/501 |
| 5,073,484 A | 12/1991 | Swanson | 435/7.92 |
| 5,591,645 A | 1/1997 | Rosenstein | 436/514 |
| 5,654,162 A | 8/1997 | Guire | 435/7.92 |
| 5,656,503 A | 8/1997 | May | 436/514 |
| 5,712,172 A | 1/1998 | Huang | 436/518 |
| 5,714,389 A | 2/1998 | Charlton | 436/27 |
| 5,877,028 A | 3/1999 | Chandler | 436/514 |
| 6,020,147 A | 2/2000 | Guire | 435/7.92 |
| 6,096,563 A | 8/2000 | Hudak | 436/523 |
| 6,194,221 B1 | 2/2001 | Rehg | 436/514 |
| 6,271,046 B1 | 8/2001 | Chandler | 436/530 |
| 6,485,982 B1 | 11/2002 | Charlton | 436/514 |
| 6,565,808 B2 | 5/2003 | Hudak | 422/411 |
| 7,270,959 B2 | 9/2007 | Hudak | 435/7.1 |
| 7,300,633 B2 | 11/2007 | Hudak | 422/537 |
| 7,749,775 B2* | 7/2010 | Maher et al. | 436/518 |
| 2002/0058031 A1 | 5/2002 | Hudak | 422/140.1 |
| 2003/0008410 A1* | 1/2003 | Hechinger | 436/172 |
| 2003/0016897 A1* | 1/2003 | Walt et al. | 385/12 |
| 2008/0194044 A1* | 8/2008 | Faris et al. | 436/537 |

OTHER PUBLICATIONS

Dickson et al., Journal of Photochemistry and Photobiology. 27 (1995) 3-19.*

(Continued)

*Primary Examiner* — Chris L Chin

(74) *Attorney, Agent, or Firm* — Foley & Lardner LLP

(57) ABSTRACT

The present invention includes an assay method for detecting an analyte in a sample. The assay includes a solid surface such as a nitrocellulose membrane. It also includes providing a sample is applied to the solid surface and detecting the presence or absence of the analyte using a fluorescent label from a lanthanide label. The invention also includes a device for detecting the fluorescence in or on an assay test strip. The device includes a housing, a solid surface and an ultraviolet radiation emitting LED.

20 Claims, 4 Drawing Sheets

A = Anti *P.f.* Malaria Capture Antibody
(*P.f.* capture region)

B = Anti Pan Malaria Capture Antibody
(Pan capture region)

C = Anti-Mouse (Control) Capture Antibody
(Control region)

(56) References Cited

OTHER PUBLICATIONS

Multiplexing DELFIA assays using lanthanide-labeled probes. pp. 1-8.*

Peruski et al., Clinical and Diagnostic Laboratory Immunology. Jul. 2003. p. 506-513.*

Hemmila, "Luminescent lanthanide chelates—a way to more sensitive diagnostic methods," Journal of Alloys and Compounds, 225:480-485 (1995).

Vuojola et al., "Resonance energy transfer from lanthanide chelates to overlapping and nonoverlapping fluorescent protein acceptors," Anal. Chem. 81:5033-5038 (2009). Abstract Only.

Xiao et al., "Quantum yields of luminescent lanthanide chelates and far-red dyes measured by resonance energy transfer." J. Am. Chem. Soc., 123:7067-7073 (2001).

Materials relating to Sofia Fluorescent Immunoassay Analyzer obtained from Quidel www page on Dec. 24, 2011 (www.quidel.com).

* cited by examiner

A = Anti *P.f.* Malaria Capture Antibody
(*P.f.* capture region)

B = Anti Pan Malaria Capture Antibody
(Pan capture region)

C = Anti-Mouse (Control) Capture Antibody
(Control region)

A = Anti-Thyroxine Capture Antibody (Test region)

B = Anti-BSA (Control) Capture Antibody (Control region)

A = Avidin, Streptavidin, Neutravidin or anti-biotin (Test region)

B = Anti-mouse Capture Antibody (Control region)

USE OF NON-CHELATED FLUOROCHROMES IN RAPID TEST SYSTEMS

CROSS REFERENCE TO RELATED APPLICATIONS

The present invention claims benefit of priority to U.S. provisional patent application Ser. No. 61/005,301, filed on Dec. 3, 2007, which is incorporated herein by reference in its entirety.

TECHNICAL FIELD

The present invention relates to the field of diagnostic tests, and in particular to the field of rapid diagnostic tests such as but not limited to, lateral flow test strips.

BACKGROUND

Rapid diagnostic tests allow one to detect the presence of antibody, antigen, metabolite toxin or other substance in a sample. Common applications include diagnosing diseases and detecting drugs, biological entities or harmful agents. In addition to being accurate, the tests are preferably easy to use, self-contained and user-friendly without requiring expensive laboratory instruments or training. Currently available tests lack sensitivity or require expensive laboratory equipment thus requiring improvement.

Presently available rapid diagnostic tests often use a colored particle, dye or enzymatic color-producing reaction to generate a visible test result. Such tests are often unsuitable for detecting low levels of a target analyte. Other diagnostics use fluorescence. However, fluorescent tests are laboratory based because the fluorochromes used in them have small stokes shifts which require sophisticated and expensive instruments to analyze the emission light. These tests use time-resolved fluorescence to obtain quantitative results.

The present invention uses fluorochromes with a large stokes shift. This eliminates the need for laboratory instruments to differentiate the excitation from emission light. The test system greatly enhances the detection level of counterpart color-developing systems, provides a concise result and can be inexpensively produced.

SUMMARY

Figure 1:
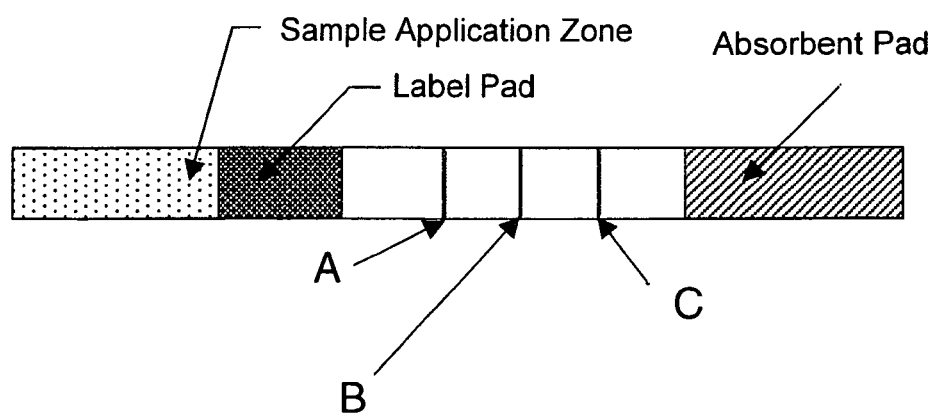
FIG. 1 depicts of one aspect of the invention using a nitrocellulose test strip wherein anti-P.f. malaria antibodies are striped onto the P.f. capture region of the strip (A). Anti-pan malaria antibodies are striped onto the strip as the capture entity in the Pan capture region (B). The anti-mouse antibody is included in the control region of the strip (C).

The present invention recognizes that current diagnostic test systems that rely on color-producing tests may not provide detection levels low enough to correctly diagnose the status of certain physiological conditions. Using fluorescent detectors can increase the sensitivity of such tests but requires expensive laboratory equipment. Diagnostic tests can utilize superior detection levels and faster and clearer signal development if alternative signal generation chemistry were used.

A first aspect of the present invention is an assay method for detecting an analyte in a sample. A sample is applied to a solid surface, such as a nitrocellulose membrane. An analyte is detected using a lanthanide label such as europium. It is an improvement over currently available tests because it uses lanthanide labels that have a large stokes shift. This increases the sensitivity of the tests and does not require expensive laboratory equipment.

A second aspect of the invention is a device for detecting fluorescence on an assay test strip. The devise includes a housing, a solid surface and an ultraviolet radiation emitting LED The user places a test strip under the device which exposes it to the proper wavelength of UV light and causes the label to fluoresce. A quantitative assay is also achievable with the use of a low cost reader that would be able to quantitate the emission light. An emission light analysis circuit can be added to the reader to accomplish this task.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture procedures for devices and components described below are well known and commonly employed in the art. Conventional methods are used for these procedures, such as those provided in the art and various general references. Where a term is provided in the singular, the plural of that term is also contemplated. The nomenclature used herein and the laboratory procedures described below are those well known and commonly employed in the art. As employed throughout the disclosure, the following terms, unless otherwise indicated, shall be understood to have the following meanings.

A "component" of a sample or "sample component" is any constituent of a sample, and can be an ion, molecule, compound, molecular complex, organelle, virus, bacteria, cell, aggregate, or particle of any type, including colloids, aggregates, particulates, crystals, minerals, etc. A component of a sample can be soluble or insoluble in the sample media or a provided sample buffer or sample solution. A component of a sample can be in gaseous, liquid, or solid form. A component of a sample may be a moiety or may not be a moiety.

A "moiety" or "moiety of interest" is any entity whose manipulation is desirable. A moiety can be a solid, including a suspended solid, or can be in soluble form. A moiety can be a molecule. Molecules that can be manipulated include, but are not limited to, inorganic molecules, including ions and inorganic compounds, or can be organic molecules, including amino acids, peptides, proteins, glycoproteins, lipoproteins, glycolipoproteins, lipids, fats, sterols, sugars, carbohydrates, nucleic acid molecules, small organic molecules, or complex organic molecules. A moiety can also be a molecular complex, can be an organelle, can be one or more cells, including prokaryotic and eukaryotic cells, or can be one or more etiological agents, including viruses, bacteria, parasites, or prions, or portions thereof. A moiety can be a crystal, mineral, colloid, fragment, mycelle, micelle, droplet, bubble, or the like, and can comprise one or more inorganic materials such as polymeric materials, metals, minerals, glass, ceramics, and the like. Moieties can also be aggregates of molecules, complexes, cells, organelles, viruses, bacteria, etiological agents, crystals, colloids, or fragments. Cells can be any cells, including prokaryotic and eukaryotic cells. Eukaryotic cells can be of any type. Of particular interest are cells such as, but not limited to, white blood cells, malignant cells, stem cells, progenitor cells, fetal cells, and cells infected with an etiological agent, and bacterial cells. Moieties can also be artificial particles such polystyrene microbeads made of polystyrene or other polymer compositions, magnetic microbeads, particles of polystyrene or other polymer compositions, microspheres of polystyrene or other polymer compositions, and carbon microbeads.

"Binding partner" refers to any substances that both bind to the moieties with desired affinity or specificity and are manipulatable with the desired physical force(s). Non-limiting examples of the binding partners include cells, cellular organelles, viruses, bacteria, microparticles or an aggregate or complex thereof, or an aggregate or complex of molecules.

A "microparticle," "microbead" or "particle" is a structure of any shape and of any composition that is manipulatable by desired physical force(s). The microparticles used in the methods could have a dimension from about 0.01 micron to about 10 centimeters. Preferably, the microparticles used in the methods can be comprised of any suitable material, such as glass or ceramics, and/or one or more polymers, such as, for example, nylon, polytetrafluoroethylene, polystyrene, polyacrylamide, sepharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated or micromachined particles, etc.

"Coupled" means bound. For example, a moiety can be coupled to a microparticle by specific or nonspecific binding. As disclosed herein, the binding can be covalent or noncovalent, reversible or irreversible. As used herein, "the moiety to be manipulated is substantially coupled onto surface of the binding partner" means that a percentage of the moiety to be manipulated is coupled onto surface of the binding partner and can be manipulated by a suitable physical force via manipulation of the binding partner.

A "specific binding member" is one of two different molecules having an area on the surface or in a cavity which specifically binds to and is thereby defined as complementary with a particular spatial and chemical organization of the other molecule. A specific binding member can be a member of an immunological pair such as antigen-antibody, antibody-antibody, protein-protein, lectin-antigen, biotin-avidin, biotin-streptavidin, biotin-neutravidin, ligand-receptor, nucleic acid duplexes, Ig-protein A, Ig-protein G, Ig-protein L, Ig-protein A/G, DNA-DNA, DNA-RNA, RNA-RNA, or the like.

An "antibody" is an immunoglobulin molecule, and can be, as nonlimiting example, an IgG, an IgM, an IgE, an IgA or other type of immunoglobulin molecule. As used herein, "antibody" also refers to a portion of an antibody molecule that retains the binding specificity of the antibody from which it is derived (for example, single chain antibodies or Fab fragments).

A "fluid sample" is any fluid from which components are to be separated or analyzed. A sample can be from any source, such as from an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample, or a wash of an internal area of the body.

"Selectively binds" means that a specific binding member used in the methods of the present invention to remove one or more undesirable sample components does not appreciably bind to rare cells of interest of the sample. The term "does not appreciably bind" means that not more than 30%, preferably not more than 20%, more preferably not more than 10%, and yet more preferably not more than 1.0% of one or more rare cells of interest are bound by the specific binding member used to remove non-RBC undesirable components from the fluid sample. In many cases, the undesirable components of a blood sample will be white blood cells. In preferred embodiments of the present invention, a combined solution of the present invention can be used for sedimenting red blood cells and selectively removing white blood cells from a blood sample.

A "binding assay" is an assay that tests for the presence or concentration of an entity by detecting binding of the entity to a specific binding member, or that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the presence, concentration, or activity of one or more components of a sample.

"Lateral flow test strips" are known in the art, for example, see U.S. Pat. No. 7,384,796 B2 by Davis, et al., which is incorporated by reference herein.

A "LED" is a light-emitting diode that is known in the art.

Other technical terms used herein have their ordinary meaning in the art that they are used, as exemplified by a variety of technical dictionaries.

Introduction

As a non-limiting introduction to the breath of the present invention, the present invention includes several general and useful aspects, including:
1) an assay method for detecting an analyte in a sample wherein a sample is contacted with a solid surface and an analyte is detected using fluorescence; and
2) a device that includes a housing, a solid surface and an ultraviolet radiation emitting LED for detecting fluorescence in or on an assay test strip.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I. Method for Detecting an Analyte in a Sample

The present invention includes an assay method for detecting an analyte in a sample. The assay includes a solid surface such as a nitrocellulose membrane. It also includes providing a sample is applied to the solid surface and detecting the presence or absence of the analyte using a fluorescent label from a lanthanide label.

The lanthanide label can be, for example, europium, samarium, terbium or dysprosium. Other labels useful in the present invention are, for example, a phycoerythrin or a chlorophyll B. The lanthanide label can be europium. The lanthanide label can also be bound to a specific binding member. The binding member can be an antibody or an active fragment thereof. The sensitivity of the assay can be improved by linking the lanthanide label is to on or in a particle. Latex particles can be any color or white. The fluorescent label or the binding member can be covalently or non-covalently linked to the particles.

The assay is can be carried out as a competitive assay or a non-competitive format, or a homogenous or heterogeneous format. The assay can be used as a qualitative test wherein the user achieves a "yes" or "no" answer based on the presence or absence of fluorescence. The assay is can also be qualitative or quanititative with the use of a by analyzing the intensity of the emission light.

The solid surface is analyzed with an ultraviolet radiation emitting LED. The ultraviolet radiation causes the label to fluoresence. Preferably, the user looks for the fluorescent signal under the UV light of appropriate wavelength. The solid surface used in the assay can be a test II. Device for Detecting Fluorescence in or on an Assay Test Strip The invention also includes a device for detecting the fluorescence in or on an assay test strip. The device includes a housing, a solid surface and an ultraviolet radiation emitting LED. The test strip may include a lanthanide. The device emits UV light of appropriate wavelength to view the lanthanide. The device can be used to view europium, samarium, terbium, dysprosium, phycoerythrin or chlorophyll B. The lanthanide can be europium.

The lanthanide can be bound to a specific binding member. The specific binding member can be an antibody or an active fragment thereof. The lanthanide can be bound to, on or in a particle. The solid surface can be a test strip such as a nitrocellulose membrane.

Rapid diagnostic tests (e.g. lateral flow tests, flow through tests, and immunochromatographic tests) are color-producing diagnostic that are designed to be easy to use, self contained, user-friendly, instrument-free systems. Currently available tests have successfully been adapted to permit the user to apply a sample, wait a prescribed time and then read the resultant color visually without the aid of instrumentation. However, the typical current visual test systems may not provide detection levels low enough to correctly diagnose the status of certain physiological conditions. Such conditions may require a detection level that is lower than that generated by these color-producing tests. Many tests could enjoy superior detection levels and faster and clearer signal development if alternative signal generation chemistry were used.

Typical rapid tests use a colored particle, dye or enzymatic color-producing reaction to generate a visible test result. The use of molecules that emit light have been used mostly in quantitative, laboratory-based immunoassay/immunochemistry diagnostic tests. This is primarily due to the need for an expensive and complex fluorimeter, luminometer or spectrophotometer to analyze the wavelength and intensity of the light emitted by these molecules. Light-emitting molecules enhance the detection level of immunoassay/immunochemistry-based tests because the amount of light they generate is greater than the amount of color generated by the colored or color-producing moieties.

Fluorochromes are molecules that when exposed to one wavelength of light (known as the excitation wavelength) emit a different wavelength of light (known as the emission wavelength). This is known as fluorescence. Flurochromes have a range of wavelengths of light in which the molecule is excited. Within this range of wavelengths, there is one at which excitation is optimal. Therefore, a plot of wavelength versus excitation would yield a peak. Generally, the optimal wavelength is referred to as the "excitation" wavelength, although any wavelength of light within the peak will cause the molecule to fluoresce. The fluorescence light produced, known as the emission light, is also a band of light that exists as a peak.

A Stokes shift is the difference in the wavelength of the emission light from the excitation light. Fluorochromes available and used in immunoassay/immunochemistry-based tests have a very small Stokes shift. When the fluorochrome has a small stokes shift, the excitation and emission peaks may overlap. For example, the fluorochrome fluorescein has an excitation peak from about 450 nanometers (nm) to 530 nm, with the optimal excitation wavelength of about 495 nm. It has an emission light peak from about 480 nm to 570 nm, with an optimal emission wavelength of about 519 nm. From optimal excitation to optimal emission, the Stokes shift is only 24 nm and the excitation and emission peaks overlap. Because of this narrow Stokes shift, the emission light must be analyzed at a specific wavelength to differentiate it from excitation light. The only way to effectively discern emission light from excitation light is by using light wavelength filters that allow a small range of emission light to pass or to use an instrument such as a fluorimeter or spectrophotometer to accurately analyze a specific wavelength of light. Neither technique is cost effective for a "point of care test" because the test is expensive and may require a trained operator to maintain and operate the laboratory equipment.

In the present invention, lanthanides (europium, samarium, terbium, dysprosium), and phycoerythrin and chlorophyll B are used as fluorochromes. These molecules have stokes shifts greater than 100 nm and their excitation and emission peaks do not overlap. This means that the excitation light is different than the emission light and is discernible visually, thus eliminating the need for an expensive filter or instrument to differentiate excitation from emission light. This allows them to be integrated into a low cost test system that incorporates easy-to-use viewers and readers, making the use of these molecules very practical for point of care tests.

The present inventions incorporates a test design and construction to be used with an inexpensive viewer. The viewer safely provides the excitation light and allows the user to observe the emission light. The label or light-producing reagent used as the label (europium, samarium, terbium, dysprosium, phycoerythrin and chlorophyll B, to name a few) in immunoassay or immunochemistry-type tests is easily visible with the viewer. This system greatly enhances the detection level of the target molecule compared to color-producing tests, retains the simplicity and cost effectiveness found in the current color-producing tests and is well suited for point-of-care or single-use tests.

The present invention uses the traditional principles used in immunoassays wherein a target molecule binds to and/or is bound by a specific binding element or elements. The assay can be either a competitive or non-competitive assay, for example. The label material comprises one or more of the fluorochromes mentioned above. In one aspect, sample is applied to the test strip along with any required reagents and the test strip is allowed to run for its prescribed time. The result is observed by placing the test in a simple viewing apparatus. This apparatus houses a LED light source that emits a specific wavelength light and the user is able to observe the emission light. For simplicity, a lateral flow-type test using an Europium label is described in the embodiments. However, any target molecule/binding element type assay/test or any of the fluorochromes and their associated viewers (with LEDs with appropriate excitations wavelengths) can be used.

Europium, for example, has an excitation peak from about 320-380 nm and an emission peak from about 600-620 nm. The user places the test strip in the viewer and activates the UV light. This allows the user to view the emission light and determine the presence or absence of the Europium label, thus determining the test result.

The viewer is comprised of a housing, a power source, a pulsation circuit, a switch, a viewing window, a light source with a light diffuser and a test strip/device platform. UV LEDs (light emitting diodes) that emit light at about 365 nm wavelength are used as the light source. Other wavelengths of light can be used based on the characteristics of the label or labels being used. A LED light pulsing circuit is used that overdrives the LEDs, thus providing higher light output while allowing them to cool prior to applying the next power surge. This allows the LEDs to emit a stronger light without prematurely burning out. The power source is comprised of "button" batteries. A momentary switch is used to activate the LEDs. The case is preferably made of an opaque material, typically plastic. The view window is made of a plastic that does not substantially allow UV light of wavelength shorter than 385 nm to pass. This material is typically found in safety eyeglasses. In addition, this window can be tinted orange to eliminate any auto-fluorescence from the blue (365 nm) excitation light and increase the visual contrast of the emission light.

The user inserts the test strip or test housing into the opening of the viewer and onto the strip/device platform. The strip or device is pushed along the platform until it stops, thus positioning the test line region(s) and control line region directly underneath the viewing window. The user then depresses the switch which activates the LEDs. The light emitted from the LEDs passes through the diffusers to minimize "hot-spots" and direct the light to the region underneath the viewing window. Although the LEDs pulsate, the pulsation is too fast to be discerned by the human eye.

If Europium is contained on the test or control lines, the Europium will fluoresce and produce a red colored (about 615 nm) light. The user determines the result of the test, ceases to depress the switch thereby turning off the LEDs and removes the strip or device from the reader. The reader may be re-used with additional test strips or devices. The viewer is preferably designed so that the batteries may be replaced when depleted. This reader emits potentially harmful UV light in the interior of the device so the user should not disassemble the viewer or look directly at the LEDs. However, the reader is designed such that the user cannot see the LEDs without disassembling the viewer.

EXAMPLES

Example #1

Lateral Flow Non-Competitive Assay

Lateral flow (immunochromatographic) tests are usually designed with several key components, including but not limited to a sample application zone, a label zone, a mixing zone, a detection zone and an absorbent zone. In this aspect, we describe a non-competitive immunoassay wherein a target molecule is captured by a binding element. A second binding element that also binds to the target molecule is used as the label or detection element. In the case of target molecule with a recurring/repeating epitope (binding site), for example a virus, the first and second binding elements may be the same entity, however the second element will be labeled with the detection molecule.

As a working example, we describe a P.f. malaria/pan malaria combination test. This tests uses a pair of complimentary monoclonal (mouse) antibodies to detect the malaria type *Plasmodium falciparum* (P.f.) and a pair of antibodies to detect all four malaria types (pan malaria). It also uses an anti-mouse antibody for the procedural control line.

One of the anti-P.f. malaria antibodies is striped onto the nitrocellulose as the capture entity in the P.f. capture region of the nitrocellulose strip. One of the anti-pan malaria antibodies is striped onto the nitrocellulose as the capture entity in the Pan capture region of the nitrocellulose strip. The anti-mouse antibody is striped onto the nitrocellulose as the capture entity in the control region of the nitrocellulose strip. A Europium chelate is bound to the complimentary (second) anti-P.f. malaria antibody. The lanthanides are attached to the antibodies using a chelator. The phycoerythrin and chlorophyll B can be bound covalently to the antibody via amino, carboxyl or sulfihdryl attachments.

The same Europium chelate is also bound to the complimentary (2) anti-pan malaria antibody. These Europium chelated antibodies are diluted to a working concentration in a label pad solution, are sprayed onto the label pad and dried. The label pad solution is formulated to allow the Europium chelated antibodies to migrate along the strip upon rehydration. The strip is constructed as diagrammed in FIG. 1. The strip can then either be used as a "dipstick" or placed in a housing.

Figure 4:
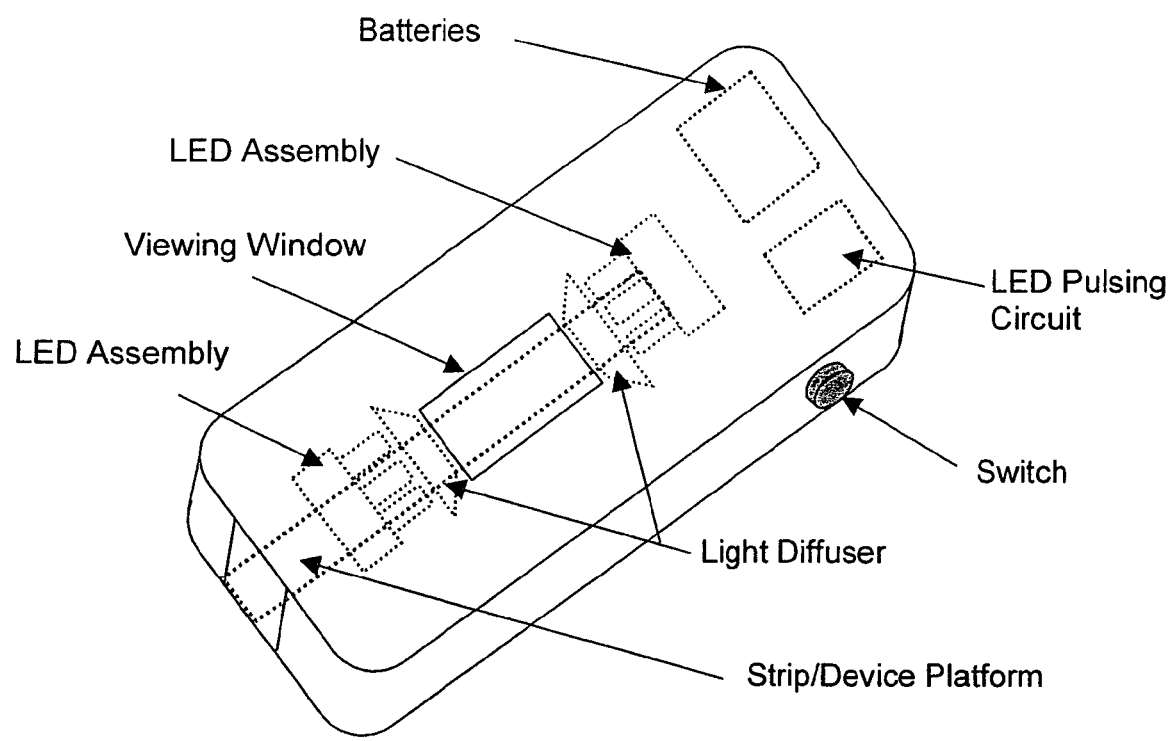
FIG. 4 depicts one aspect of strip/device viewer for use with the invention. The viewer is composed of a housing, a power source, a pulsation circuit, a switch, a viewing window, a light source w/light diffuser and a test strip/device platform.

For this aspect, we describe the dipstick format. Sample is placed onto the sample application zone. Approximately four drops of a lysing/wash solution (approximately 100 micro liters) are placed into a test tube. The strip is added to the tube so the sample pad comes in contact with the lysing/wash solution in the test tube. As the solution flow up the strip, it encounters the sample and mixes with it and continues to migrate up the strip. If malaria antigen is present in the sample, the Europium chelated antibodies bind to the antigen. This europium chelated antibody/antigen complex continues to migrate up the strip where it will be captured by the appropriate complimentary capture antibody. This forms a line in either (or both) the P.f. or Pan malaria capture region. Excess or unbound Europium chelated antibody is captured by the control capture antibody, forming a line in the control region. After the prescribed time, the strip is removed from the tube and placed in the viewer (or the strip can be exposed to the appropriate wavelength of excitation light) and the results are observed. A viewer is illustrated in FIG. 4.

Example #2

This aspect is similar to example #1, except after the Europium is chelated to the antibodies, the Europium chelated antibodies are coupled, either passively or covalently, to white latex particles with a diameter ranging from about 200 to about 600 nm. This can be achieved by placing the particles in an organic solvent in the presence of Europium and then drying down the particles. The organic solvent causes the particles to swell by having the solvent fill voids in the matrix. Upon evaporation, the Europium stays in the space while the organic evaporates.

This process amplifies the signal because a single antigen bound to the capture line and to the particle will now have several Europium molecules immobilized to it via the particle. The Europium chelated antibodies can be coupled individually, either passively or covalently, to the white latex particles. Then the Europium chelated antibody-particles can be mixed to the appropriate working ratio, or the Europium chelated antibodies can be blended into an appropriate working ratio and then coupled, either passively or actively, to the latex particles.

The strip configuration remains the same, but here the Europium chelated antibody-particles are diluted to a working concentration in a label pad solution and are sprayed onto the label pad and dried. The procedure for using the strip and observing the results is the same.

Example #3

In this aspect, Europium is embedded in, or attached to the latex particles in a fashion that still allows a protein molecule (in this case an antibody) to be coupled to it, either passively or covalently. Therefore, the particle itself is the Europium label. The antibody does not have a Europium chelate coupled to it. The strip configuration remains the same as embodiment #2, except now the antibody coupled Europium particles are diluted to a working concentration in a label pad solution and are sprayed onto the label pad and dried. The procedure for using the strip and observing the results is the same.

Example #4

Lateral Flow Competitive Assay

In this embodiment, we describe a competitive immunoassay. A target molecule is captured by a binding element. The target molecule, or a hapten of the target molecule is used as the label or detection element. As a working example, we describe a competitive thyroxin test. This test uses an antibody to capture thyroxin in the sample, and a thyroxin hapten (thyroxin-BSA) as the label. In this test, anti-thyroxin is striped onto the nitrocellulose as the capture entity in the test line region of the strip. Anti-BSA is striped onto the nitrocellulose as the capture entity in the control line region of the strip. A Europium chelate is coupled to Thyroxin-BSA. The Europium chelated Thyroxin-BSA is diluted to a working concentration in a label pad solution sprayed onto the label pad and dried. The label pad solution is formulated to allow the Europium chelated Thyroxin-BSA to migrate along the strip upon rehydration. The strip can then either be used as a "dipstick" or placed in a housing.

Figure 2:
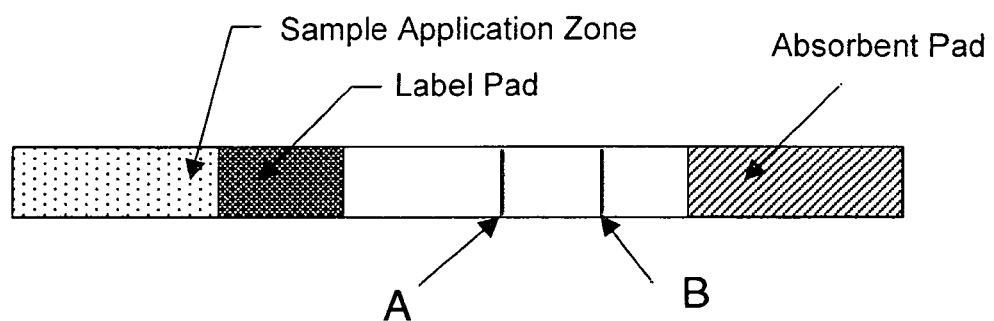
FIG. 2 depicts of one aspect of the invention using a nitrocellulose test strip wherein anti-thyroxine antibodies are striped a capture region of the strip (A). Anti-BSA antibodies are striped onto the strip as the capture entity in the control region (B).

For this example, we describe the dipstick format as shown in FIG. 2. Sample is placed onto the sample application zone. Approximately four drops of a lysing/wash solution (approximately 100 µl) are placed into a test tube. The strip is added to the tube so the sample pad comes in contact with the lysing/wash solution in the test tube. As the solution flows up the strip, it encounters the sample and mixes with it and continues to migrate up the strip. If Thyroxin antigen is present in the sample, it competes with the Europium chelated Thyroxin-BSA for the limited number of binding sites on the capture antibody. Therefore, if no thyroxin antigen is present in the sample, a line will form in the capture zone. The intensity of the line will decrease as the thyroxin antigen concentration increases in the sample. Excess or unbound Europium chelated Thyroxin-BSA will be captured by the control capture antibody, forming a line in the control region. After the prescribed time, the strip is removed from the tube and placed into the viewer (or the strip can be exposed to the appropriate wavelength of excitation light) and the results are observed.

Example #5

This aspect is similar to example #4, but after the Europium is chelated to the Thyroxin-BSA, the Europium chelated Thyroxin-BSA is coupled, either passively or covalently, to latex particles with a diameter ranging from about 200 to about 600 nm. This amplifies the signal because a single Europium chelated Thyroxin-BSA molecule bound to the capture line and to the particle will now have several Europium molecules immobilized to it via the particle.

The strip configuration remains the same but the Europium chelated Thyroxin-BSA-particles are diluted to a working concentration in a label pad solution and are sprayed onto the label pad and dried. The procedure for using the strip and observing the results is the same.

Example #6

In this aspect, Europium is embedded in, or attached to the latex particles in a fashion that still allows a protein molecule (in this case the Thyroxin-BSA) to be coupled to it, either passively or covalently. Therefore, the particle itself is the Europium label. The Thyroxin-BSA does not have a Europium chelate coupled to it. The strip configuration remains the same as described in example #5, but here the Thyroxin-BSA coupled Europium particles are diluted to a working concentration in a label pad solution and are sprayed onto the label pad and dried. The procedure for using the strip and observing the results is the same.

Example #7

Lateral Flow Non-Competitive Assay

Figure 3:
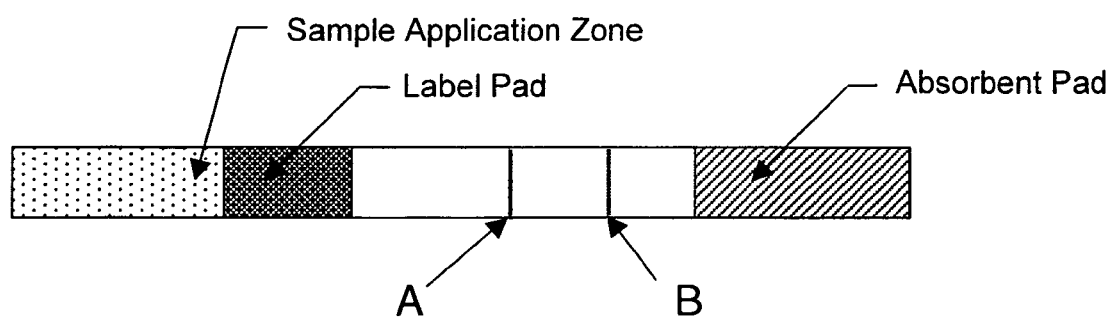
FIG. 3 depicts one aspect of the invention using a nitrocellulose test strip wherein avidin, streptavidin, neutravidin or anti-biotin antibodies are striped onto the capture region of the strip (A). Anti-mouse antibodies are striped onto the strip as the capture entity in the Pan capture region (B).

In this aspect, we describe a non-competitive immunoassay. A target molecule is bound to a first binding element that is biotinylated. A second binding element that also binds to the target molecule is used as the label or detection element. In the case of target molecule with a recurring/repeating epitope (binding site), for example a virus, the first and second binding elements may be the same entity. However the first element will be biotinylated and the second element will be labeled with the detection molecule. As a working example, a P.f. malaria test is described as shown in FIG. 3. This test uses a pair of complimentary monoclonal (mouse) antibodies to detect the malaria type *Plasmodium falciparum* (P.f.). It also uses an anti-mouse antibody for the procedural control line.

One of the anti-P.t malaria antibodies is biotinylated. Avidin, streptavidin, neutravidin or anti-biotin antibody is striped onto the nitrocellulose as the capture entity in the test capture region of the nitrocellulose strip. The anti-mouse antibody is striped onto the nitrocellulose in the control region of the nitrocellulose strip. A Europium chelate is bound to the complimentary anti-P.f. malaria antibody. This Europium chelated antibody along with the anti-P.f. biotinylated antibody are diluted to their working concentration in a label pad solution, sprayed onto the label pad and dried. The label pad solution is formulated to allow the Europium chelated antibody to migrate along the strip upon rehydration. The strip can then either be used as a "dipstick" or placed in a housing.

For this example, the dipstick format is described. Sample is placed onto the sample application zone. Approximately four drops of a lysing/wash solution (approximately 100 μl) are placed into a test tube. The strip is added to the tube so the sample pad comes in contact with the lysing/wash solution in the test tube. As the solution flow up the strip, it encounters the sample and mixes with it and continues to migrate up the strip. If malaria P.f. antigen is present in the sample, the Europium chelated antibody and the complimentary anti P.f.-biotin capture antibody bind to the antigen. This Europium chelated antibody/antigen/antibody-biotin complex continues to migrate up the strip where it will be captured by the avidin or streptavidin, neutravidin or anti-biotin. This will form a line in the test region. Excess or unbound Europium chelated antibody will be captured by the control capture antibody, forming a line in the control region. After the prescribed time, the strip is removed from the tube and placed into the viewer (or the strip can be exposed to the appropriate wavelength of excitation light) and the results observed.

Example #8

This aspect is similar to example #7, except after the Europium is chelated to the anti P.f. antibody, the Europium chelated antibody is coupled, either passively or covalently, to latex particles with a diameter ranging from about 200 to about 600 nm. This amplifies the signal because a single antigen bound to the capture line and to the particle will now have several Europium molecules immobilized to it via the particle. The strip configuration remains the same, but now the Europium chelated antibody-particles are diluted to a working concentration in a label pad solution and are sprayed onto the label pad and dried. The procedure for using the strip and observing the results is the same.

Example #9

In this aspect, Europium is embedded in, or attached to the latex particles in a fashion that still allows a protein molecule (in this case an antibody) to be coupled to it, either passively or covalently. Therefore, the particle itself is the Europium label. The antibody does not have a Europium chelate coupled to it. The strip configuration remains the same as described in aspect #2, but the antibody coupled Europium particles are diluted to a working concentration in a label pad solution are sprayed onto the label pad and dried. The procedure for using the strip and observing the results is the same.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. An assay method for detecting the presence of an analyte in a sample, the method comprising:
   a) providing a test strip comprising:
      i) a label pad, said label pad comprising a plurality of particles having a plurality of lanthanide fluorochrome molecules embedded therein, and a binding member or a hapten of the analyte bound to the particle, said binding member capable of binding to the analyte, wherein said lanthanide fluorochrome molecules are not chelated;
      ii) a detection zone in fluid contact with the label pad, said detection zone comprising a first capture entity immobilized within the detection zone, said first capture entity capable of binding the analyte or the hapten, and
      iii) optionally a control zone comprising a second capture entity capable of binding the hapten or the binding member;
   b) contacting the test strip with the sample, said sample comprising or suspected of comprising the analyte;
   c) incubating the test strip for a prescribed period of time, said period of time being sufficient for the binding member and the first and/or second capture entities to bind the analyte and/or the hapten;
   d) exposing the test strip to a source of ultraviolet radiation to excite the lanthanide fluorochrome molecules; and
   e) detecting an emission from the lanthanide fluorochrome molecules in the detection zone, wherein the presence of the analyte is correlated to the emission from the lanthanide fluorochrome molecules in the detection zone.

2. The assay method of claim 1, wherein said source of ultraviolet radiation to excite said fluorochrome on or in a particle is provided by a LED.

3. The assay method of claim 1, wherein said source of ultraviolet radiation emits a wavelength of between about 320 nM and about 380 nM.

4. The assay method of claim 3, wherein said source of ultraviolet radiation emits a wavelength of about 365 nM.

5. The assay method of claim 1, wherein said lanthanide fluorochrome is selected from the group consisting of europium, samarium, terbium and dysprosium.

6. The assay method of claim 5, wherein said lanthanide fluorochrome comprises europium.

7. The assay method of claim 5, wherein said lanthanide fluorochrome comprises samarium.

8. The assay method of claim 5, wherein said lanthanide fluorochrome comprises terbium.

9. The assay method of claim 5, wherein said lanthanide fluorochrome comprises dysprosium.

10. The assay method of claim 1, wherein said binding member comprises an antibody, an active fragment of an antibody, a nucleic acid, an antigen, a lectin, a protein, biotin, avidin, streptavidin, neutravidin, a ligand, a receptor, a small molecule, an organic molecule, an inorganic molecule, an organelle a virus, a cell or a combination thereof.

11. The assay method of claim 1, wherein said particle comprises a polymer.

12. The assay method of claim 1, wherein said assay is a lateral flow assay.

13. The assay method of claim 1, wherein said assay is an immunochromatographic assay.

14. The method of claim 1 which is a non-competitive assay, wherein the binding member is bound to the particles such that the presence of the analyte is indicated by emission from the lanthanide fluorochrome molecules in the detection zone.

15. The method of claim 1 which is a competitive assay, wherein the hapten of the analyte is bound to the particles such that the presence of the analyte is indicated by a decreased emission intensity from the lanthanide fluorochrome molecules in the detection zone.

16. The method of claim 1, wherein the emission from the lanthanide fluorochrome molecules is visually discernible without the use of a filter or instrument to differentiate excitation from emission light.

17. The method of claim 1, said lanthanide fluorochrome molecules having a stokes shift of greater than 100 nm.

18. The method of claim 1, wherein the intensity of the emission light is quantitated by a reader.

19. The method of claim 1, further comprising applying a reagent to the test strip.

20. The method of claim 1, wherein the particles are made of glass, metal, latex, ceramic, carbon, or a polymer.

* * * * *